United States Patent
Himmelsbach et al.

(10) Patent No.: US 6,403,580 B1
(45) Date of Patent: Jun. 11, 2002

(54) QUINAZOLINES, PHARMACEUTICAL COMPOSITIONS CONTAINING THESE COMPOUNDS, THEIR USE AND PROCESSES FOR PREPARING THEM

(75) Inventors: Frank Himmelsbach, Mittelbiberach; Elke Langkopf, Warthausen; Birgit Jung, Schwabenheim; Stefan Blech, Warthausen, all of (DE); Flavio Solca, Vienna (AT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/935,498

(22) Filed: Aug. 23, 2001

Related U.S. Application Data
(60) Provisional application No. 60/230,541, filed on Sep. 5, 2000.

(30) Foreign Application Priority Data

Aug. 26, 2000 (DE) .......................... 100 42 064

(51) Int. Cl.$^7$ ................. A61K 31/517; A61K 31/5377; C07D 413/12; C07D 239/94
(52) U.S. Cl. ................ 514/230.8; 514/234.5; 514/259; 544/119; 544/293
(58) Field of Search ............... 514/234.5, 259, 514/230.8; 544/119, 293

(56) References Cited

U.S. PATENT DOCUMENTS
5,760,041 A  6/1998  Wissner et al.

FOREIGN PATENT DOCUMENTS

| EP | 0 787 722 A1 | 8/1997 |
|----|---|---|
| WO | WO96 33980 A1 | 10/1996 |
| WO | WO97 30035 A1 | 8/1997 |
| WO | WO97 32856 A1 | 9/1997 |
| WO | WO 97 38983 | 10/1997 |
| WO | WO98 13354 A1 | 4/1998 |
| WO | WO 99 01467 | 1/1999 |
| WO | WO99 06378 A | 2/1999 |
| WO | WO99 09016 A1 | 2/1999 |
| WO | WO00 18740 A1 | 4/2000 |
| WO | WO00 31048 A | 6/2000 |
| WO | WO00 51991 A | 9/2000 |
| WO | WO00 55141 A1 | 9/2000 |

OTHER PUBLICATIONS

Smaill, J. B., et al, "Tyrosine Kinase Inhibitors. 17. Irreversible Inhibitors of the Epidermal Growth Factor Receptor: 4–(Phenylamino)quinazoline– and 4–(Phenylamino)pyrido[3,2–d]pyrimidine–6–acrylamides Bearing Additional Solubilizing Functions", J. Med. Chem (2000), 43(7), 1380–1397.

Boschelli; "Small molecule inhibitors of receptor tyrosine kinases"; Review Article—Chemical Sciences.

*Primary Examiner*—Joseph K. McKane
*Assistant Examiner*—Rebecca Anderson
(74) *Attorney, Agent, or Firm*—Robert P. Raymond; Alan R. Stempel; Mary-Ellen M. Devlin

(57) ABSTRACT

Quinazolines of the formula

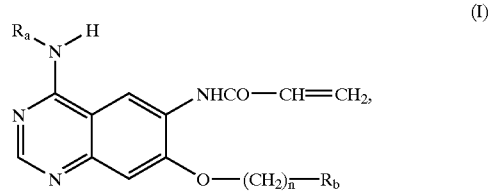

having an inhibitory effect on signal transduction mediated by tyrosine kinases, the use thereof for treating diseases, particularly tumoral diseases, diseases of the lungs and respiratory tract, and the preparation thereof.

8 Claims, No Drawings

1

QUINAZOLINES, PHARMACEUTICAL COMPOSITIONS CONTAINING THESE COMPOUNDS, THEIR USE AND PROCESSES FOR PREPARING THEM

RELATED APPLICATIONS

Benefit of U.S. Provisional Application Ser. No. 60/230,541, filed on Sep. 5, 2000 is hereby claimed.

FIELD OF THE INVENTION

The present invention relates to quinazolines of general formula

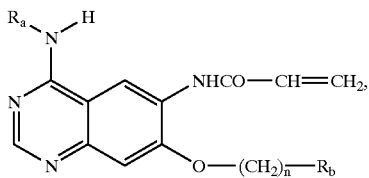

(I)

the tautomers, the stereoisomers and the salts thereof, particularly the physiologically acceptable salts thereof with inorganic or organic acids or bases which have valuable pharmacological properties, particularly an inhibitory effect on signal transduction mediated by tyrosine kinases, the use thereof for treating diseases, particularly tumoral diseases, diseases of the lungs and respiratory tract, and the preparation thereof.

In the above general formula I $R_a$ denotes a benzyl or 1-phenylethyl group or a phenyl group substituted by the groups $R_1$ and $R_2$, wherein $R_1$ denotes a hydrogen, fluorine, chlorine or bromine atom, a methyl, trifluoromethyl, cyano or ethynyl group and $R_2$ denotes a hydrogen or fluorine atom, $R_b$ denotes an —N(CH$_2$CO$_2$R$_3$)$_2$-group, wherein $R_3$ denotes a hydrogen atom, a methyl or ethyl group, a R$_4$O—CO—CH$_2$—N—CH$_2$—CH$_2$—OH group optionally substituted at the methylene groups by 1 or 2 methyl or ethyl groups, wherein $R_4$ denotes a hydrogen atom or a $C_{1-4}$-alkyl group, a 2-oxo-morpholin-4-yl-group which may be substituted by 1 or 2 methyl or ethyl groups, or a N-(2-oxo-tetrahydrofuran-4-yl)-methylamino-group and n denotes an integer in the range from 2 to 4, Preferred compounds of the above general formula I are the above, with the exception of the compound 4-[(3-bromophenyl)amino]-7-[3-(2-oxo-morpholin-4-yl)propyloxy]-6-[(vinylcarbonyl)amino]-quinazoline, the tautomers, the stereoisomers and the salts thereof.

Particularly preferred compounds are the abovementioned compounds of general formula I wherein $R_a$ denotes a 1-phenylethyl group or a phenyl group substituted by the groups $R_1$ and $R_2$, wherein $R_1$ denotes a fluorine, chlorine or bromine atom, a methyl or ethynyl group and $R_2$ denotes a hydrogen or fluorine atom, $R_b$ denotes a 2-oxo-morpholin-4-yl-group which is substituted by 1 or 2 methyl or ethyl groups, or a N-(2-oxo-tetrahydrofuran-4-yl)-methylamino-group and n denotes an integer in the range from 2 to 4, the tautomers, the stereoisomers and the salts thereof.

Most particularly preferred compounds are the compounds of the above general formula I wherein $R_a$ denotes a 1-phenylethyl- or 3-chloro-4-fluorophenyl group, $R_b$ denotes a 2-oxo-morpholin-4-yl-group which is substituted by 1 or 2 methyl groups, and n denotes an integer from the range from 2 to 4, the tautomers, the stereoisomers and the salts thereof.

The following particularly preferred compounds of general formula I may be mentioned by way of example:

(1) 4-[(R)-(1-phenyl-ethyl)amino]-7-[2-(2,2-dimethyl-6-oxo-morpholin-4-yl)-ethoxy]-6-[(vinylcarbonyl)amino]-quinazoline, (2) 4-[(3-chloro-4-fluoro-phenyl)amino]-7-[3-((S)-6-methyl-2-oxo-morpholin-4-yl)-propyloxy]-6-[(vinylcarbonyl)amino]-quinazoline, (3) 4-[(3-chloro-4-fluoro-phenyl)amino]-7-[3-(2,2-dimethyl-6-oxo-morpholin-4-yl)-propyloxy]-6-[(vinylcarbonyl)amino]-quinazoline, (4) 4-[(3-chloro-4-fluoro-phenyl)amino]-7-[2-(2,2-dimethyl-6-oxo-morpholin-4-yl)-ethoxy]-6-[(vinylcarbonyl)amino]-quinazoline, (5) 4-[(3-chloro-4-fluoro-phenyl)amino]-7-[3-((R)-6-methyl-2-oxo-morpholin-4-yl)-propyloxy]-6-[(vinylcarbonyl)amino]-quinazoline, (6) 4-[(3-chloro-4-fluoro-phenyl)amino]-7-[2-((R)-6-methyl-2-oxo-morpholin-4-yl)-ethoxy]-6-[(vinylcarbonyl)amino]-quinazoline, (7) 4-[(3-chloro-4-fluoro-phenyl)amino]-7-[2-((S)-6-methyl-2-oxo-morpholin-4-yl)-ethoxy]-6-[(vinylcarbonyl)amino]-quinazoline, (8) 4-[(3-chloro-4-fluoro-phenyl)amino]-7-[4-((S)-3-methyl-2oxo-morpholin-4-yl)-butyloxy]-6-[(vinylcarbonyl)amino]-quinazoline and (9) 4-[(3-chloro-4-fluoro-phenyl)amino]-7-[4-((R)-6-methyl-2-oxo-morpholin-4-yl)-butyloxy]-6-[(vinylcarbonyl)amino]-quinazoline, the tautomers, the stereoisomers and the salts thereof.

The compounds of general formula I may be prepared by the following methods, for example:

a) reacting a compound of general formula

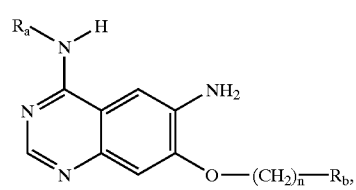

(II)

wherein $R_a$, $R_b$ and n are as hereinbefore defined, with a compound of general formula

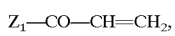

(III)

wherein $Z_1$ denotes a leaving group such as a halogen atom, e.g. a chlorine or bromine atom, a vinylcarbonyloxy group or a hydroxy group.

The reaction is optionally carried out in a solvent or mixture of solvents such as methylene chloride, dimethylformamide, acetonitrile, toluene, chlorobenzene, tetrahydrofuran, methylene chloride/tetrahydrofuran or dioxane optionally in the presence of an inorganic or organic base and optionally in the presence of a dehydrating agent, expediently at temperatures between −80 and 150° C., preferably at temperatures between −60 and 80° C.

With a compound of general formula III wherein $Z_1$ denotes a leaving group, the reaction is optionally carried out in a solvent or mixture of solvents such as methylene chloride, dimethylformamide, acetonitrile, toluene, chlorobenzene, tetrahydrofuran, methylene chloride/tetrahydrofuran or dioxane conveniently in the presence of a tertiary organic base such as triethylamine or N-ethyl-diisopropylamine (Hünig base), while these organic bases may simultaneously serve as solvent, or in the presence of an inorganic base such as sodium carbonate, potassium carbonate or sodium hydroxide solution, expediently at temperatures between −80 and 150° C., preferably at temperatures between −60 and 80° C.

With a compound of general formula III wherein $Z_1$ denotes a hydroxy group, the reaction is preferably carried out in the presence of a dehydrating agent, e.g. in the presence of isobutyl chloroformate, thionyl chloride, trimethylchloro-silane, phosphorus trichloride, phosphorus pentoxide, hexamethyldisilazane, N,N'-dicyclohexyl carbodiimide, N,N'-dicyclohexyl carbodiimide/N-hydroxysuccinimide or 1-hydroxy-benzotriazole and optionally additionally in the presence of 4-dimethylamino-pyridine, N,N'-carbonyldiimidazole or triphenylphosphine/carbon tetrachloride, conveniently in a solvent such as methylene chloride, tetrahydrofuran, dioxane, toluene, chlorobenzene, dimethylsulphoxide, ethylene glycol diethyl ether or sulpholane and optionally in the presence of a reaction accelerator such as 4-dimethylaminopyridine at temperatures between −80 and 150° C., but preferably at temperatures between −60 and 80° C.

However, it is particularly advantageous to carry out the reaction with acrylic acid and acrylic acid chloride in the presence of triethylamine.

In the reactions described hereinbefore, any reactive groups present such as hydroxy, carboxy or imino groups may be protected during the reaction by conventional protecting groups which are cleaved again after the reaction.

For example, a protecting group for a hydroxy group may be a trimethylsilyl, acetyl, benzoyl, methyl, ethyl, tert.butyl, trityl, benzyl or tetrahydropyranyl group, a protecting group for a carboxyl group may be a trimethylsilyl, methyl, ethyl, tert.butyl, benzyl or tetrahydropyranyl group and protecting groups for an imino group may be a formyl, acetyl, trifluoroacetyl, ethoxycarbonyl, tert.butoxycarbonyl, benzyloxycarbonyl, benzyl, methoxybenzyl or 2,4-diethoxybenzyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethylether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

The compounds of general formulae II to III used as starting materials are known from the literature in some cases or may be obtained by methods known per se from the literature (see. Examples I to X).

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosine kinase itself It is also possible that the transmission of signals t o components located further down is blocked.

The biological properties of the new compounds were investigated as follows:

The inhibition of EGF-R-mediated signal transmission can be demonstrated e.g. with cells which express human EGF-R and whose survival and proliferation depend on stimulation by EGF or TGF-alpha. A cell line of murine origin dependent on interleukin-3-(IL-3) which was genetically modified to express functional human EGF-R was used here. The proliferation of these cells known as F/L-HERc can therefore be stimulated either by murine IL-3 or by EGF (cf. von Rüden, T. et al. in EMBO J . 7, 2749–2756 (1988) and Pierce, J. H. et al. in Science 239, 628–631 (1988)).

The starting material used for the F/L-HERc cells was the cell line FDC-$P_1$, the production of which has been described by Dexter, T. M. et al. in J. Exp. Med. 152, 1036–1047 (1980). Alternatively, however, other growth-factor-dependent cells may also be used (cf. for example Pierce, J. H. et al. in Science 239, 628–631 (1988), Shibuya, H. et al. in Cell 70, 57–67 (1992) and Alexander, W. S. et al. in EMBO J. 10, 3683–3691 (1991)). For expressing the human EGF-R cDNA (cf Ullrich, A. et al. in Nature 309, 418–425 (1984)) recombinant retroviruses were used as described by von Rüden, T. et al., EMBO J. 7, 2749–2756 (1988), except that the retroviral vector LXSN (cf. Miller, A. D. et al. in BioTechniques 7, 980–990 (1989)) was used for the expression of the EGF-R cDNA and the line GP+E86 (cf. Markowitz, D. et al. in J. Virol. 62, 1120–1124 (1988)) was used as the packaging cell.

The test was performed as follows:

F/L-HERc cells were cultivated in RPMI/1640 medium (BioWhittaker), supplemented with 10 % foetal calf serum (FCS, Boehringer Mannheim), 2 mM glutamine (BioWhittaker), standard antibiotics and 20 ng/ml of human EGF (Promega), at 37° C. and 5% $CO_2$. In order to investigate the inhibitory activity of the compounds according to the invention, $1.5 \times 10^4$ cells per well were cultivated in triplicate in 96-well dishes in the above medium (200 µl), the cell proliferation being stimulated with either EGF (20 ng/ml) or murine IL-3. The IL-3 used was obtained from culture supernatants of the cell line X63/0 mIL-3 (cf. Karasuyama, H. et al. in Eur. J. Immunol. 18, 97–104 (1988)). The compounds according to the invention were dissolved in 100% dimethylsulphoxide (DMSO) and added to the cultures in various dilutions, the maximum DMSO concentration being 1%. The cultures were incubated for 48 hours at 37° C.

In order to determine the inhibitory activity of the compounds according to the invention the relative cell number was measured in O.D. units using the Cell Titer 96™ Aqueous Non-Radioactive Cell Proliferation Assay (Promega). The relative cell number was calculated as a percentage of the control (F/LHERc cells without inhibitor) and the concentration of active substance which inhibits the proliferation of the cells by 50% ($IC_{50}$) was derived therefrom. The following results were obtained:

| Compound (Example No.) | Inhibition of the EGF-dependent proliferation $IC_{50}$ [nM] |
|---|---|
| 1(2) | 0.4 |

The compounds of general formula I according to the invention thus inhibit the signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation of tyrosine kinases, e.g. in inflammatory diseases of the airways such as chronic bronchitis, chronic obstructive bronchitis, asthma, bronchiectasias, allergic or non-allergic rhinitis or sinusitis, cystic fibrosis, $\alpha$1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas and protein loss syndrome, also for treating nasal polyps and polyps of the gastrointestinal tract of various origins, such as for example villous or adenomatous polyps of the large bowel, but also polyps in familial polyposis coli, intestinal polyps in Gardner's syndrome, polyps throughout the entire gastrointestinal tract in Peutz-Jeghers Syndrome, inflammatory pseudopolyps, juvenile polyps, colitis cystica profunda and pneumatosis cystoides intestinales.

Moreover, the compounds of general formula I and the physiologically acceptable salts thereof may be used to treat kidney diseases, particularly cystic changes as in cystic kidneys, for treating renal cysts which may be idiopathic in origin or which occur in syndromes such as e.g. tubercular sclerosis, in von-Hippel-Lindau Syndrome, in nephronophthisis and spongy kidney and other diseases caused by abnormal functioning of tyrosine kinases such as e.g. epidermal hyperproliferation (psoriasis), inflammatory processes, diseases of the immune system, hyperproliferation of haematopoietic cells, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. For treating respiratory tract diseases, these compounds may be used on their own or in conjunction with other therapeutic agents for the airways, such as substances with a secretolytic, broncholytic and/or anti-inflammatory activity. For treating diseases in the region of the gastrointestinal tract, these compounds may also be administered on their own or in conjunction with substances having an effect on motility or secretion or with anti-inflammatory substances. These combinations may be administered either simultaneously or sequentially.

These compounds may be administered either on their own or in conjunction with other active substances by intravenous, subcutaneous, intramuscular, intrarectal, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:
Preparation of the starting products:

EXAMPLE I 6-amino4-[(3-chloro-4-fluoro-phenyl)amino]-7-[3-(2,2-dimethyl-6-oxo-morpholin-4-yl)-propyloxy]-quinazoline 308 mg of 4-[(3-chloro-4-fluoro-phenyl)amino]-7-[3-(2,2-dimethyl-6-oxo-morpholin-4-yl)-propyloxy]-6-nitro-quinazoline and 145 mg of iron powder are suspended in 15 ml of ethanol and heated to boiling. The suspension is combined with 0.38 ml of glacial acetic acid and 0.30 ml of water with heating. After about 1.5 hours the reduction is complete. For working up the solvent is distilled off in vacuo using a rotary evaporator. The residue is taken up in methylene chloride, combined with a few small ice chips and made alkaline with 2 ml of 4N sodium hydroxide solution. The organic phase is separated off and the dark aqueous phase is extracted with methylene chloride/methanol (95:5). The combined organic phases are dried over magnesium sulphate and evaporated down. The crude product is reacted further without any additional purification.

Yield: 267 mg (92% of theory), $R_f$ value: 0.32 (silica gel, methylene chloride/methanol=95:5)

Mass spectrum (ESI⁻): m/z=472, 474 [M–H]⁻
The following products are obtained analogously to Example I:
(1) 6-amino-4-[(3-chloro-4-fluoro-phenyl)amino]-7-[2-(2,2-dimethyl-6-oxo-morpholin-4-yl)-ethoxy]-quinazoline $R_f$ value: 0.47 (silica gel, methylene chloride/methanol/concentrated aqueous ammonia solution=90:10:0.1)

Mass spectrum (ESI⁻): m/z=458, 460 [M–H]⁻
(2) 6-amino-4-[(R)-(1-phenyl-ethyl)amino]-7-[2-(2,2-dimethyl-6-oxo-morpholin-4-yl)-ethoxy]-quinazoline $R_f$ value: 0.23 (silica gel, methylene chloride/methanol=95:5)

Mass spectrum (ESI⁻): m/z=434 [M–H]⁻
(3) 6-amino-4-[(3-chloro-4-fluoro-phenyl)amino]-7-[3-((S)-6-methyl-2-oxo-morpholin-yl)-propyloxy]-quinazoline $R_f$ value: 0.31 (silica gel, methylene chloride/methanol=95:5)

Mass spectrum (ESI⁺): m/z=460, 462 [M+H]⁺
(4) 6-amino-4-[(R)-(1-phenyl-ethyl)amino]-7-(2-{N,N-bis-[(methoxycarbonyl)methyl]-amino}-ethoxy)-quinazoline $R_f$ value: 0.22 (silica gel, methylene chloride/methanol=95:5)

Mass spectrum (ESI⁺): m/z=468 [M+H]⁺
(5) 6-amino-4-[(3-chloro-4-fluoro-phenyl)amino]-7-[3-((R)-6-methyl-2-oxo-morpholin-4yl)-propyloxy]-quinazoline $R_f$ value: 0.31 (silica gel, methylene chloride/methanol=95:5)

Mass spectrum (ESI⁻): m/z=458, 460 [M–H]⁻
(6) 6-amino-4-[(3-chloro-4-fluoro-phenyl)amino]-7-[2-((R)-6-methyl-2-oxo-morpholin-4-yl)-ethoxy]-quinazoline $R_f$ value: 0.23 (silica gel, methylene chloride/methanol=95:5)

Mass spectrum (ESI⁻): m/z=444, 446 [M–H]⁻
(7) 6-amino-4-[(3 -chloro-4-fluoro-phenyl)amino]-7-[2-((S)-6-methyl-2-oxo-morpholin-4yl)-ethoxy]-quinazoline $R_f$ value: 0.23 (silica gel, methylene chloride/methanol=95:5)

Mass spectrum (ESI⁻): m/z=444, 446 [M–H]⁻
(8) 6-amino-4-[(3-chloro-4-fluoro-phenyl)amino]-7-[4-((S)-3-methyl-2-oxo-morpholin-4yl)-butyloxy]-quinazoline $R_f$ value: 0.59 (silica gel, methylene chloride/methanol/concentrated, aqueous ammonia solution=90:10:0.1)

Mass spectrum (ESI⁻): m/z=472, 474 [M–H]⁻
(9) 6-Amino-4-[(3-chloro-4-fluoro-phenyl)amino]-7-(2-{N-[(tert.-butyloxycarbonyl)methyl]-N-(1,1-dimethyl-2-hydroxy-ethyl)-amino}-ethoxy)-quinazoline $R_f$ value: 0.50 (silica gel, methylene chloride/methanol=9:1)

Mass spectrum (ESI⁻): m/z=532, 534 [M–H]⁻

EXAMPLE II

4-[(3-chloro-4-fluoro-phenyl)amino]-7-[3-(2,2-dimethyl-6-oxo-morpholin-4-yl)-propyloxy]-6-nitro-quinazoline 152 mg of potassium carbonate and 100 mg of sodium iodide are added to 500 mg of 4-[(3-chloro-4-fluoro-phenyl)amino]-7-(3-methanesulphonyloxy-propyloxy)-6-nitro-quinazoline and 0.21 ml of diisopropylethylamine in 10 ml of acetonitrile. Then 561 mg of ethyl (2-hydroxy-2-methyl-propylamino)-acetate are added and the reaction mixture is refluxed for about seven hours. For working up the reaction mixture is evaporated down. The residue is stirred with copious amounts of ethyl acetate, washed with a little cold water and saturated sodium chloride solution, dried over magnesium sulphate and evaporated down. Since clearly a mixture of open-chain and already cyclised product has formed, the resin-like residue is refluxed with 0.08 ml of acetyl chloride in 40 ml of ethanol for about 30 minutes. The mixture is then evaporated down and the residue is combined with toluene. The solvent is distilled off and the flask residue is suspended in methylene chloride, combined with a little ice-water and made alkaline with 1 ml of 4N sodium hydroxide solution. The organic phase is separated off, dried over magnesium sulphate and evaporated down. The residue is chromatographed through a silica gel column with methylene chloride/methanol (98:2). The desired product is stirred with a little tert.butylmethylether, suction filtered and dried. The lactone is obtained as a yellowish solid.

Yield: 129 mg (24% of theory),
$R_f$ value: 0.32 (silica gel, ethyl acetate)
Mass spectrum (ESI$^-$): m/z=502, 504 [M–H]$^-$ The following products are obtained analogously to Example II:

(1) 4-[(3-chloro-4-fluoro-phenyl)amino]-7-[2-(2,2-dimethyl-6-oxo-morpholin-4-yl)-ethoxy]-6-nitro-quinazoline (The cyclised product is obtained straight away, therefore no after-treatment is required)
$R_f$ value: 0.38 (silica gel, ethyl acetate)
Mass spectrum (ESI$^-$): m/z=488, 490 [M–H]$^-$ (2) 4-[(R)-(1-phenyl-ethyl)amino]-7-[2-(2,2-dimethyl-6-oxo-morpholin-4-yl)-ethoxy]-6-nitro-quinazoline (The product mixture obtained initially is converted into the cyclised product by after-treatment with p-toluenesulphonic acid in toluene)
$R_f$ value: 0.45 (silica gel, methylene chloride/methanol=95:5)
Mass spectrum (ESI$^-$): m/z=464 [M–H]$^-$ (3) 4-[(3-chloro-4-fluoro-phenyl)amino]-7-[3-((S)-6-methyl-2-oxo-morpholin-4-yl)-propyloxy]-6-nitro-quinazoline (The cyclised product is obtained straight away, therefore no after-treatment is required)
$R_f$ value: 0.37 (silica gel, methylene chloride/methanol=95:5)
Mass spectrum (ESI$^-$): m/z=488, 490 [M–H]$^-$ (4) 4-[(R)-(1-phenyl-ethyl)amino]-7-(2-{N,N-bis[(methoxy-carbonyl)methyl]-amino}-ethoxy)-6-nitro-quinazoline (the reaction is carried out in N,N-dimethylformamide. No after-treatment is carried out)
$R_f$ value: 0.31 (silica gel, methylene chloride/methanol=95:5)
Mass spectrum (ESI$^-$): m/z=496 [M–H]$^-$ (5) 4-[(3-chloro-4-fluoro-phenyl)amino]-7-[4-((S)-3-methyl-2-oxo-morpholin-4-yl)-butyloxy]-6-nitro-quinazoline (No after-treatment is carried out. The starting material ethyl (S)-2-(2-hydroxy-ethylamino)-propionate is obtained by reacting ethyl (R)-2-(trifluoromethylsulphonyloxy)-propionate with 2-amino-ethanol in methylene chloride)
$R_f$ value: 0.73 (silica gel, methylene chloride/methanol=9:1)
Mass spectrum (ESI$^-$): m/z=502, 504 [M–H]$^-$ (6) 4-[(3-chloro-4-fluorophenyl)amino]-7-(2-{N-[(tert.-butyloxycarbonyl)methyl]-N-(1,1-dimethyl-2-hydroxy-ethyl)-amino}-ethoxy)-6-nitro-quinazoline
$R_f$ value: 0.46 (silica gel, ethyl acetate)

(7) 4-[(3-chloro-4-fluorophenyl)amino]-7-(3-{N-[(tert.-butyloxycarbonyl)methyl]-N-(1,1-dimethyl-2-hydroxy-ethyl)-amino}-propyloxy)-6-nitro-quinazoline
$R_f$ value: 0.31 (silica gel, methylene chloride/methanol=95:5)
Mass spectrum (ESI$^-$): m/z=576, 578 [M–H]$^-$ (8) 4-[(3-chloro-4-fluorophenyl)amino]-7-{2-[N-(2-oxo-tetrahydrofuran-4-yl)-N-methyl-amino]-ethoxy}-6-nitro-quinazoline
(The preparation of the starting material 4-methylamino-2-oxo-tetrahydrofuran has already been described elsewhere: WO 0055141 A1)
Melting point: 214–215.5° C.
Mass spectrum (ESI$^+$): m/z=476, 478 [M+H]$^+$ (9) 4-[(3-chloro-4-fluorophenyl)amino]-7-(4-{N-[(tert.-butyloxycarbonyl)methyl]-N-(1,1-dimethyl-2-hydroxy-ethyl)-amino}-butyloxy)-6-nitro-quinazoline
$R_f$ value: 0.44 (silica gel, ethyl acetate)
Mass spectrum (ESI$^-$): m/z=590, 592 [M–H]$^-$

(10) 4-[(3-chloro-4-fluorophenyl)amino]-7-(4-{N-[(tert.-butyloxycarbonyl)methyl]-N-((R)-2-hydroxy-prop-1-yl)-amino}-butyloxy)-6-nitro-quinazoline
$R_f$ value: 0.33 (silica gel, methylene chloride/methanol=95:5)
Mass spectrum (ESI$^+$): m/z=578, 580 [M+H]$^+$

(11) 4-[(3-chloro-4-fluorophenyl)amino]-7-(4-{N-[(tert.-butyloxycarbonyl)methyl]-N-((S)-2-hydroxy-prop-1-yl)-amino}-butyloxy)-6-nitro-quinazoline
$R_f$ value: 0.33 (silica gel, methylene chloride/methanol=95:5)
Mass spectrum (ESI$^+$): m/z=578, 580 [M+H]$^+$

(12) 4-[(3-chloro-4-fluorophenyl)amino]-7-(4-{N-[(ethoxycarbonyl)methyl]-N-(2-hydroxy-2-methyl-prop-1-yl)-amino}-butyloxy)-6-nitro-quinazoline
$R_f$ value: 0.40 (silica gel, methylene chloride/methanol=95:5)

(13) 4-[(3-chloro-4-fluorophenyl)amino]-7-{3-[N-(2-oxo-tetrahydrofuran-4-yl)-N-methyl-amino]-propyloxy}-6-nitro-quinazoline
$R_f$ value: 0.23 (silica gel, methylene chloride/methanol=95:5)
Mass spectrum (ESI$^+$): m/z=490, 492 [M+H]$^+$

EXAMPLE III

4-[(3-chloro-4-fluoro-phenyl)amino]-7-(3-methanesulphonyloxy-propyloxy)-6-nitro-quinazoline 0.96 ml of methanesulphonic acid chloride are added dropwise to 4.60 g of 4-[(3-chloro-4-fluoro-phenyl)amino]-7-(3-hydroxy-propyloxy)-6-nitro-quinazoline and 4.29 ml of diisopropylethylamine in 150 ml of methylene chloride at ambient temperature with stirring. The reaction mixture is stirred for about 30 minutes at ambient temperature, then another 0.1 ml of methanesulphonic acid chloride are added. After about one hour the reaction is complete and the cloudy reaction solution is combined with ice-water. A thick yellowish precipitate is formed which is suction filtered, washed with a little methylene chloride and water and dried in the desiccator.

Yield: 5.06 g (92% of theory),
$R_f$ value: 0.43 (silica gel, methylene chloride/methanol=95:5)
Mass spectrum (ESI$^-$): m/z=469, 471 [M–H]$^-$ The following products are obtained analogously to Example III:

(1) 4-[(3-chloro-4-fluoro-phenyl)amino]-7-(2-methanesulphonyloxy-ethoxy)-6-nitro-quinazoline
$R_f$ value: 0.53 (silica gel, methylene chloride/methanol/concentrated aqueous ammonia solution=90:10:1)
Mass spectrum (ESI$^-$): m/z=455, 457 [M–H]$^-$ (2) 4-[(R)-(1-phenyl-ethyl)amino]-7-(2-methanesulphonyloxy-ethoxy)-6-nitro-quinazoline
$R_f$ value: 0.45 (silica gel, methylene chloride/methanol=95:5)
Mass spectrum (ESI$^-$): m/z=431 [M–H]$^-$ (3) 4-[(3-chloro-4-fluoro-phenyl)amino]-7-(4-methanesulphonyloxy-butyloxy)-6-nitro-quinazoline
$R_f$ value: 0.82 (silica gel, methylene chloride/methanol=9:1)
Mass spectrum (ESI$^-$): m/z=483, 485 [M–H]$^-$

EXAMPLE IV

4-[(3-chloro-4-fluoro-phenyl)amino]-7-(3-hydroxy-propyloxy)-6-nitro-quinazoline 3.00 ml of concentrated hydrochloric acid are added dropwise to 21.30 g of 4-[(3-chloro-4-fluoro-phenyl)

amino]-7-[3-(tetrahydropyran-2-yloxy)-propyloxy]-6-nitro-quinazoline in 200 ml of methanol. A yellow precipitate is formed. The suspension is stirred for about another 3.5 hours at 50° C. For working up the methanol is distilled off in vacuo using a rotary evaporator. The residue is combined with ethyl acetate and some ice-water and made alkaline with sodium hydroxide solution. The organic phase is washed with water and saturated sodium chloride solution and left to stand overnight at ambient temperature, whereupon a yellow precipitate is formed. This is suction filtered, washed with ethyl acetate and dried. The filtrate is evaporated down and the evaporation residue is recrystallised from ethyl acetate. The crystals thus obtained are combined with the previously suction filtered precipitate and again recrystallised from ethyl acetate. The desired product is obtained in the form of slightly yellowish crystals.

Yield: 4.60 g (40% of theory), melting point: 224–227° C.

Mass spectrum (ESI⁻): m/z=391, 393 [M–H]⁻

The following products are obtained analogously to Example IV:

(1) 4-[(3-chloro-4-fluoro-phenyl)amino]-7-(2-hydroxy-ethoxy)-6-nitro-quinazoline
$R_f$ value: 0.46 (silica gel, methylene chloride/methanol/concentrated aqueous ammonia solution=90:10:1)
Mass spectrum (ESI⁻): m/z=377, 379 [M–H]⁻

(2) 4-[(R)-(1-phenyl-ethyl)amino]-7-(2-hydroxy-ethoxy)-6-nitro-quinazoline
melting point: 192–194° C.
Mass spectrum (ESI⁻): m/z=353 [M–H]⁻

(3) 4-[(3-chloro-4-fluoro-phenyl)amino]-7-(4-hydroxy-butyloxy)-6-nitro-quinazoline
$R_f$ value: 0.70 (silica gel, methylene chloride/methanol=9:1)
Mass spectrum (ESI⁻): m/z=405, 407 [M–H]⁻

EXAMPLE V

4-[(3-chloro-4-fluoro-phenyl)amino]-7-[2-(tetrahydropyran-2-yloxy)-ethoxy]-6-nitro-quinazoline 3.64 g of sodium hydride (60%) are added batchwise to 13.00 g of 2-(tetrahydropyran-2-yloxy)-ethanol in 250 ml of tetrahydrofuran while cooling with an ice bath. Then the reaction mixture is heated to about 30–40° C. in a water bath and stirred for 15 minutes. It is then cooled again in the ice bath and combined with 15.60 g of 4-[(3-chloro-4-fluoro-phenyl)amino]-7-fluoro-6-nitro-quinazoline in 50 ml of tetrahydrofuran. The reaction mixture immediately turns dark red. After 10 minutes the ice bath is removed and the reaction mixture is stirred for one hour at ambient temperature. Then a total of 1.00 g of sodium hydride is added and stirring is continued for a further 1.5 hours at 50° C. until the reaction is complete. For working up about 200 ml of tetrahydrofuran are distilled off using a rotary evaporator. The residue is added to 1 litre of ice-water and neutralised with citric acid. The aqueous phase is extracted thoroughly with ethyl acetate. The combined organic phases are washed with 250 ml of semi-saturated sodium chloride solution, dried over magnesium sulphate and evaporated down. A yellow precipitate is formed, which is suction filtered and dried in the desiccator. The mother liquor is again evaporated down. The solid yellowish flask residue is triturated with tert.butyl methyl ether, suction filtered and also dried in the desiccator.

Yield: 18.93 g (88% of theory), $R_f$ value: 0.60 (silica gel, petroleum ether/ethyl acetate 1:2)

Mass spectrum (ESI⁻): m/z=461, 463 [M–H]⁻

The following products are obtained analogously to Example V:

(1) 4-[(3-chloro-4-fluoro-phenyl)amino]-7-[3-(tetrahydropyran-2-yloxy)-propyloxy]-6-nitro-quinazoline
$R_f$ value: 0.37 (silica gel, cyclohexane/ethyl acetate=1:1)
Mass spectrum (ESI⁻): m/z=475, 477 [M–H]⁻

(2) 4-[(R)-(1-phenyl-ethyl)amino]-7-[2-(tetrahydropyran-2-yloxy)-ethoxy]-6-nitro-quinazoline
$R_f$ value: 0.12 (silica gel, cyclohexane/ethyl acetate=1:1)
Mass spectrum (ESI⁻): m/z=437 [M–H]⁻

(3) 4-[(3-chloro-4-fluoro-phenyl)amino]-7-[4-(tetrahydropyran-2-yloxy)-butyloxy]-6-nitro-quinazoline (the reaction is carried out with potassium-tert.butoxide in N,N-dimethylformamide)
$R_f$ value: 0.38 (silica gel, petroleum ether/ethyl acetate=1:1)
Mass spectrum (ESI⁻): m/z=489, 491 [M–H]⁻

EXAMPLE VI

Ethyl (2-hydroxy-2-methyl-propylamino)-acetate 100.00 g of sodium carbonate are added to 50.00 g of glycine ethyl ester-hydrochloride in 100ml of saturated potassium carbonate solution with cooling. The mass obtained is extracted several times with a total of about 600 ml of diethylether. The combined ether extracts are dried over sodium sulphate and evaporated to dryness. 28.60 g of glycine ethyl ester remain. This is combined with 26.00 ml of isobutylene oxide and 40 ml of absolute ethanol and heated to 90° C. for six hours in a Roth bomb. After cooling to ambient temperature the reaction mixture is evaporated down, leaving a thin runny oil.

Yield: 45.80 g (73% of theory),

Mass spectrum (ESI⁺): m/z=176 [M+H]⁺

EXAMPLE VII

Ethyl (S)-(2-hydroxy-propylamino)-acetate 3.88 ml of ethyl bromoacetate in 10 ml of acetonitrile are added dropwise to 5.00 g of (S)-(+)-1-amino-propan-2-ol and 11.32 ml of diisopropylethylamine in 40 ml of acetonitrile within 20 minutes while cooling with an ice bath. The reaction mixture is left overnight to come up to ambient temperature. For working up the reaction solution is evaporated down. The oily flask residue is dissolved in about 15 ml of water and extracted first with tert.butylmethylether, then with ethyl acetate. The extracts are washed with water and saturated sodium chloride solution, dried over magnesium sulphate and evaporated down. The light-coloured oil thus obtained is reacted further without any additional purification.

Yield: 1.53 g (27% of theory), $R_f$ value: 0.55 (silica gel, methylene chloride/methanol=9:1)

Mass spectrum (ESI⁺): m/z=162 [M+H]⁺

The following products are obtained analogously to Example VII:

(1) tert.butyl (R)-(2-hydroxy-propylamino)-acetate (the reaction is carried out in N,N-dimethylformamide)
$R_f$ value: 0.46 (silica gel, ethyl acetate/methanol=9:1)
Mass spectrum (ESI⁺): m/z=190 [M+H]⁺

(2) tert.butyl (S)-(2-hydroxy-propylamino)-acetate (the reaction is carried out in N,N-dimethylformamide)

$R_f$ value: 0.46 (silica gel, ethyl acetate/methanol=9:1)

Mass spectrum (ESI$^+$): m/z=190 [M+H]$^+$ (3) tert.butyl (2-hydroxy-1,1-dimethyl-ethylamino)-acetate (the reaction is carried out in N,N-dimethylformamide)

$R_f$ value: 0.47 (silica gel, methylene chloride/methanol/concentrated aqueous ammonia solution=90:10:0.1)

Mass spectrum (ESI$^+$): m/z=204 [M+H]$^+$

EXAMPLE VIII

4-[(R)-(1-phenyl-ethyl)amino]-6-nitro-7-fluoro-quinazoline

A solution of 74 ml of (R)-1-phenyl-ethylamine in 100 ml of dioxane is added dropwise to 108.8 g of 4-chloro-6-nitro-7-fluoro-quinazoline in 800 ml of methylene chloride while cooling with an ice bath. The reaction mixture is stirred overnight at ambient temperature. For working up it is extracted with water. The organic phase is dried over magnesium sulphate and evaporated down. The residue is purified by chromatography through a silica gel column with petroleum ether/ethyl acetate (1:1) as eluant.

Yield 52.90 g (35% of theory),

Melting point: 203° C.

EXAMPLE IX

4-[(3-chloro-4-fluoro-phenyl)amino]-7-[3-((R)-6-methyl-2-oxo-morpholin-4-yl)-propyloxy]-6-nitro-quinazoline 285 mg of 4-[(3-chloro-4-fluoro-phenyl)amino]-7-(3-{N-[(tert.butyloxycarbonyl)methyl]-N-((R)-2-hydroxy-propyl)-amino}-propyloxy)-6-nitro-quinazoline in 5 ml of acetonitrile are combined with 0.50 ml of trifluoroacetic acid and refluxed for about two hours. The reaction solution is evaporated down and the residue is taken up in methylene chloride. The solution is made alkaline with saturated potassium carbonate solution while cooling with an ice bath. The aqueous phase is extracted with methylene chloride/methanol (95:5). The combined organic phases are washed with water, dried over magnesium sulphate and evaporated down. The yellowish resin-like crude product is further reacted without any more purification.

Yield: 254 mg $R_f$ value: 0.37 (silica gel, methylene chloride/methanol=95:5)

Mass spectrum (ESI$^-$): m/z=488, 490 [M–H]$^-$

The following products are obtained analogously to Example IX:

(1) 4-[(3-chloro-4-fluoro-phenyl)amino]-7-[2-((R)-6-methyl-2-oxo-morpholin-4-yl)-ethoxy]-6-nitro-quinazoline $R_f$ value: 0.17 (silica gel, ethyl acetate)

Mass spectrum (ESI$^-$): m/z=474, 476 [M–H]$^-$ (2) 4-[(3-chloro-4-fluoro-phenyl)amino]-7-[2-((S)-6-methyl-2-oxo-morpholin-4-yl)-ethoxy]-6-nitro-quinazoline $R_f$ value: 0.18 (silica gel, ethyl acetate)

Mass spectrum (ESI$^-$): m/z=474, 476 [M–H]$^-$ (3) 4-[(3-chloro-4-fluorophenyl)amino]-7-[3-(5,5-dimethyl-2-oxo-morpholin-4-yl)-propyloxy]-6-nitro-quinazoline $R_f$ value: 0.33 (silica gel, methylene chloride/methanol=95:5)

Mass spectrum (ESI$^-$): m/z=502, 504 [M–H]$^-$ (4) 4-[(3-chloro-4-fluorophenyl)amino]-7-[4-(5,5-dimethyl-2-oxo-morpholin-4-yl)-butyloxy]-6-nitro-quinazoline $R_f$ value: 0.34 (silica gel, methylene chloride/methanol=95:5)

Mass spectrum (ESI$^-$): m/z=516, 518 [M–H]$^-$ (5) 4-[(3-chloro-4-fluorophenyl)amino]-7-[4-((R)-6-methyl-2-oxo-morpholin-4-butyloxy]-6-nitro-quinazoline $R_f$ value: 0.20 (silica gel, ethyl acetate)

Mass spectrum (ESI$^-$): m/z=502, 504 [M–H]$^-$ (6) 4-[(3-chloro-4-fluorophenyl)amino]-7-[4-((S)-6-methyl-2-oxo-morpholin-4-yl)-butyloxy]-6-nitro-quinazoline $R_f$ value: 0.21 (silica gel, ethyl acetate)

Mass spectrum (ESI$^-$): m/z=502, 504 [M–H]$^-$ (7) 4-[(3-chloro-4-fluorophenyl)amino]-7-[4-(2,2-dimethyl-6-oxo-morpholin-4-yl)-butyloxy]-6-nitro-quinazoline Melting point: 194–197° C.

Mass spectrum (ESI$^+$): m/z=518, 520 [M+H]$^+$

EXAMPLE X

4-[(3-chloro-4-fluoro-phenyl)amino]-7-(3-{N-[(tert.butyloxycarbonyl)methyl]-N-((R)-2-hydroxy-propyl)-amino}-propyloxy)-6-nitro-quinazoline 0.42 ml of triethylamine, 415 mg of potassium carbonate and 200 mg of sodium iodide are added to 1.00 g of 4-[(3-chloro-4-fluoro-phenyl)amino]-7-(3-methanesulphonyloxy-propyloxy)-6-nitro-quinazoline and 1.21 g of tert.butyl (R)-(2-hydroxy-propylamino)-acetate in 10 ml of acetonitrile. The reaction mixture is refluxed for about ten hours. For working up the inorganic salts are filtered off and washed with ethyl acetate. The filtrate is evaporated down, the flask residue is taken up in ethyl acetate and washed with water. The organic phase is washed with saturated sodium chloride solution, dried over magnesium sulphate and evaporated down. The crude product is purified by chromatography through a silica gel column with methylene chloride/methanol (98:2) as eluant.

Yield: 480 mg (40% of theory), $R_f$ value: 0.37 (silica gel, methylene chloride/methanol=95:5)

Mass spectrum (ESI$^-$): m/z=562, 564 [M–H]$^-$

The following compounds are obtained analogously to Example X:

(1) 4-[(3-chloro-4-fluoro-phenyl)amino]-7-(2-{N-[(tert.butyloxycarbonyl)methyl]-N-((R)-2-hydroxy-propyl)-amino}-ethoxy)-6-nitro-quinazoline $R_f$ value: 0.33 (silica gel, methylene chloride/methanol=95:5)

Mass spectrum (ESI$^-$): m/z=548, 550 [M–H]$^-$ (2) 4[(3-chloro-4-fluoro-phenyl)amino]-7-(2-{N-[(tert.butyloxycarbonyl)methyl]-N-((S)-2-hydroxy-propyl)-amino}-ethoxy)-6-nitro-quinazoline $R_f$ value: 0.43 (silica gel, ethyl acetate)

EXAMPLE XI

6-Amino-4-[(3-chloro-4-fluorophenyl)amino]-7-[3-(5,5-dimethyl-2-oxo-morpholin-4-yl)-propyloxy]-quinazoline The substance is obtained in a 65% yield by hydrogenating 4-[(3-chloro-4fluorophenyl)amino]-7-[3-(5,5-dimethyl-2-oxo-morpholin-4-yl)-propyloxy]-6-nitro-quinazoline in tetrahydrofuran in the presence of Raney nickel in a Parr apparatus at a partial hydrogen pressure of 50 psi.

$R_f$ value: 0.17 (silica gel, methylene chloride/methanol=95:5)

Mass spectrum (ESI$^+$): m/z=474, 476 [M+H]$^+$

The following compounds are obtained analogously to Example XI:

(1) 6-Amino-4-[(3-chloro-4-fluorophenyl)amino]-7-{2-[N-(2-oxo-tetrahydrofuran-4-yl)-N-methyl-amino]-ethoxy}-quinazoline $R_f$ value: 0.27 (silica gel, methylene chloride/methanol=9:1)

Mass spectrum (ESI$^+$): m/z=446, 448 [M+H]$^+$ (2) 6-Amino-4-[(3-chloro-4-fluorophenyl)amino]-7-[4-(5,5-dimethyl-2-oxo-morpholin-4-yl)-butyloxy]-quinazoline $R_f$ value: 0.22 (silica gel, methylene chloride/methanol=95:5)

Mass spectrum (ESI$^+$): m/z=488, 490 [M+H]$^+$ (3) 6-Amino-4-[(3-chloro-4-fluorophenyl)amino]-7-[4-((R)-6-methyl-2-oxo-morpholin-4-yl)-butyloxy]-quinazoline $R_f$ value: 0.16 (silica gel, methylene chloride/methanol=95:5)

Mass spectrum (ESI$^-$): m/z=472, 474 [M–H]$^-$ (4) 6-Amino-4-[(3-chloro-4-fluorophenyl)amino]-7-[4-((S)-6-methyl-2-oxo-morpholin-4-yl)-butyloxy]-quinazoline Melting point: 134–139° C.

Mass spectrum (ESI$^-$): m/z=472, 474 [M–H]$^-$ (5) 6-Amino-4-[(3-chloro-4-fluorophenyl)amino]-7-[4-(2,2-dimethyl-6-oxo-morpholin-4-yl)-butyloxy]-quinazoline $R_f$ value: 0.26 (silica gel, methylene chloride/methanol=95:5)

Mass spectrum (ESI$^+$): m/z=488, 490 [M+H]$^+$ (6) 6--Amino-4-[(3-chloro-4-fluorophenyl)amino]-7-{3-[N-(2-oxo-tetrahydrofuran-4-yl)-N-methyl-amino]-propyloxy}-quinazoline Mass spectrum (ESI$^-$): m/z=458, 460 [M–H]$^-$ Preparation of the final compounds:

EXAMPLE 1

4-[(3-chloro-4-fluoro-phenyl)amino]-7-[3-(2,2-dimethyl-6-oxo-morpholin-4-yl)-propyloxy]-6-[(vinylcarbonyl)amino]-quinazoline 0.47 ml of triethylamine are added to 101 mg of acrylic acid in 5 ml of tetrahydrofuran under a nitrogen atmosphere. This mixture is cooled to about −50° C. in a dry ice/acetone cooling bath and combined with 119 mg of acrylic acid chloride in 3 ml of tetrahydrofuran, whereupon a colourless precipitate is formed. The suspension is stirred for about another hour at this temperature. Then 240 mg of 6-amino-4-[(3-chloro-4-fluoro-phenyl)amino]-7-[3-(2,2-dimethyl-6-oxo-morpholin-4-yl)-propyloxy]-quinazoline in 7 ml of tetrahydrofuran are added dropwise at −55° C. The reaction mixture is left to come slowly up to −30° C. in the cooling bath. After about one hour the dry ice/acetone cooling bath is exchanged for an ice/sodium chloride cooling bath. The reaction mixture is allowed to come up to 0° C. therein. As soon as the reaction is complete, water and methylene chloride are added and the mixture is made alkaline with sodium hydroxide solution. The aqueous phase separated off is extracted again with methylene chloride and a little methanol. The combined organic extracts are washed with water, dried and evaporated down. A yellow resin remains which is chromatographed over a silica gel column with methylene chloride/methanol (98:2) as eluant. The desired product is stirred with a little tert.butylmethylether, the fine crystalline precipitate is suction filtered, washed with tert-.butylmethylether and dried at 50° C. in vacuo.

Yield: 160 mg (60% of theory), $R_f$ value: 0.42 (silica gel, methylene chloride/methanol=95:5)

Mass spectrum (ESI$^-$): m/z=526, 528 [M–H]$^-$

The following products are obtained analogously to Example 1:

(1) 4-[(3-chloro-4-fluoro-phenyl)amino]-7-[2-(2,2-dimethyl-6-oxo-morpholin-4-yl)-ethoxy]-6-[(vinylcarbonyl)amino]-quinazoline Melting point: 182.5–184° C.

Mass spectrum (ESI$^-$): m/z=512, 514 [M–H]$^-$ (2) 4-[(R)-(1-phenyl-ethyl)amino]-7-[2-(2,2-dimethyl-6-oxo-morpholin-4-yl)-ethoxy]-6-[(vinylcarbonyl)amino]-quinazoline $R_f$ value: 0.30 (silica gel, methylene chloride/methanol=95:5)

Mass spectrum (ESI$^-$): m/z=488 [M–H]$^-$ (3) 4-[(3-chloro-4-fluoro-phenyl)amino]-7-[3-((S)-6-methyl-2-oxo-morpholin-4-yl)-propyloxy]-6-[(vinylcarbonyl)amino]-quinazoline $R_f$ value: 0.38 (silica gel, methylene chloride/methanol=95:5)

Mass spectrum (ESI$^-$): m/z=512, 514 [M–H]$^-$ (4) 4-[(R)-(1-phenyl-ethyl)amino]-7-(2-{N,N-bis[(methoxycarbonyl)methyl]-amino}-ethoxy)-6-[(vinylcarbonyl)amino]-quinazoline $R_f$ value: 0.40 (silica gel, methylene chloride/methanol=95:5)

Mass spectrum (EI): m/z=521 [M]+

(5) 4-[(3-chloro-4-fluoro-phenyl)amino]-7-[3-((R)-6-methyl-2-oxo-morpholin-4-yl)-propyloxy]-6-[(vinylcarbonyl)amino]-quinazoline $R_f$ value: 0.38 (silica gel, methylene chloride/methanol=95:5)

Mass spectrum (ESI$^-$): m/z=512, 514 [M–H]$^-$ (6) 4-[(3-chloro-4-fluorophenyl)amino]-7-[2-((R)-6-methyl-2-oxo-morpholin-4-yl)-ethoxy]-6-[(vinylcarbonyl)amino]-quinazoline $R_f$ value: 0.32 (silica gel, methylene chloride/methanol=95:5)

Mass spectrum (ESI$^-$): m/z=498, 500 [M–H]$^-$ (7) 4-[(3-chloro-4-fluoro-phenyl)amino]-7-[2-((S)-6-methyl-2-oxo-morpholin-4-yl)-ethoxy]-6-[(vinylcarbonyl)amino]-quinazoline $R_f$ value: 0.32 (silica gel, methylene chloride/methanol=95:5)

Mass spectrum (ESI$^-$): m/z=498, 500 [M–H]$^-$ (8) 4-[(3-chloro-4-fluoro-phenyl)amino]-7-[4-((S)-3-methyl-2-oxo-morpholin-4-yl)-butyloxy]-6-[(vinylcarbonyl)amino]-quinazoline $R_f$ value: 0.63 (silica gel, methylene chloride/methanol/concentrated aqueous ammonia solution=90:10:0.1)

Mass spectrum (ESI$^-$): m/z=526, 528 [M–H]$^-$ (9) 4-[(3-chloro-4-fluorophenyl)amino]-7-(2-{N-[(tert.-butyloxycarbonyl)methyl]-N-(1,1-dimethyl-2-hydroxyethyl)-amino}-ethoxy)-6-[(vinylcarbonyl)amino]-quinazoline $R_f$ value: 0.22 (silica gel, methylene chloride/methanol=95:5)

(10) 4-[(3-chloro-4-fluorophenyl)amino]-7-[3-(5,5-dimethyl-2-oxo-morpholin-4-yl)-propyloxy]-6-[(vinylcarbonyl)amino]-quinazoline $R_f$ value: 0.25 (silica gel, methylene chloride/methanol=95:5)

Mass spectrum (ESI$^-$): m/z=526, 528 [M–H]$^-$

(11) 4-[(3-chloro-4-fluorophenyl)amino]-7-{2-[N-(2-oxo-tetrahydrofuran4-yl)-N-methyl-amino]-ethoxy}-6-[(vinylcarbonyl)amino]-quinazoline Melting point: 195–199° C.

Mass spectrum (ESI$^+$): m/z=500, 502 [M+H]$^+$

(12) 4-[(3-chloro-4-fluorophenyl)amino]-7-[4-(5,5-dimethyl-2-oxo-morpholin-4-yl)-butyloxy]-6-[(vinylcarbonyl)amino]-quinazoline $R_f$ value: 0.33 (silica gel, methylene chloride/methanol=95:5)

Mass spectrum (ESI$^+$): m/z=564, 566 [M+Na]$^+$

(13) 4-[(3-chloro-4-fluorophenyl)amino]-7-[4-((R)-6-methyl-2-oxo-morpholin-4-yl)-butyloxy]-6-[(vinylcarbonyl)amino]-quinazoline $R_f$ value: 0.30 (silica gel, methylene chloride/methanol=95:5)

Mass spectrum (ESI$^+$): m/z=550, 552 [M+Na]$^+$

(14) 4-[(3-chloro-4-fluorophenyl)amino]-7-[4-((S)-6-methyl-2-oxo-morpholin-4-yl)-butyloxy]-6-[(vinylcarbonyl)amino]-quinazoline Mass spectrum (ESI$^-$): m/z=526, 528 [M-H]$^-$

(15) 4-[(3-chloro-4-fluorophenyl)amino]-7-[4-(2,2-dimethyl-6-oxo-morpholin-4-yl)-butyloxy]-6-[(vinylcarbonyl)amino]-quinazoline Melting point: 110–112° C.

Mass spectrum (ESI$^-$): m/z=540, 542 [M-H]$^-$

(16) 4-[(3-chloro-4-fluorophenyl)amino]-7-{3-[N-(2-oxo-tetrahydrofuran-4-yl)-N-methyl-amino]-propyloxy}-6-[(vinylcarbonyl)amino]-quinazoline $R_f$ value: 0.22 (silica gel, methylene chloride/methanol=95:5)

Mass spectrum (ESI$^+$): m/z=514, 516 [M+H]$^+$

EXAMPLE 2

4-[(3-chloro-4-fluorophenyl)amino]-7-[2-(5,5-dimethyl-2-oxo-morpholin-4-yl)-ethoxy]-6-[(vinylcarbonyl)amino]-quinazoline The substance is obtained by refluxing 4-[(3-chloro-4-fluorophenyl)amino]-7-(2-{N-[(tert.-butyloxycarbonyl)methyl]-N-(1,1-dimethyl-2-hydroxy-ethyl)-amino}-ethoxy)-6-[(vinylcarbonyl)amino]-quinazoline with trifluoroacetic acid in acetonitrile.

$R_f$ value: 0.29 (silica gel, methylene chloride/methanol=95:5)

Mass spectrum (ESI$^+$): m/z=514, 516 [M+H]$^+$

The following compounds may be prepared analogously to the above Examples and other methods known from the literature:

(1) 4-[(3-chloro-4-fluoro-phenyl)amino]-7-[3-(5,5-dimethyl-2-oxo-morpholin-4-yl)-propyloxy]-6-[(vinylcarbonyl)amino]-quinazoline (2) 4-[(3-chloro-4-fluoro-phenyl)amino]-7-[2-(5,5-dimethyl-2-oxo-morpholin-4-yl)-ethoxy]-6-[(vinylcarbonyl)amino]-quinazoline (3) 4-[(3-chloro-4-fluoro-phenyl)amino]-7-[3-((S)-3-methyl-2-oxo-morpholin-4-yl)-propyloxy]-6-[(vinylcarbonyl)amino]-quinazoline (4) 4-[(3-chloro-4-fluoro-phenyl)amino]-7-[3-((R)-3-methyl-2-oxo-morpholin-4-yl)-propyloxy]-6-[(vinylcarbonyl)amino]-quinazoline (5) 4-[(3-bromo-phenyl)amino]-7-[3-((S)-6-methyl-2-oxo-morpholin-4-yl)-propyloxy]-6-[(vinylcarbonyl)amino]-quinazoline (6) 4-[(3-bromo-phenyl)amino]-7-[3-((R)-6-methyl-2-oxo-morpholin-4-yl)-propyloxy]-6-[(vinylcarbonyl)amino]-quinazoline (7) 4-[(3-methyl-phenyl)amino]-7-[2-((S)-6-methyl-2-oxo-morpholin-4-yl)-ethoxy]-6-[(vinylcarbonyl)amino]-quinazoline (8) 4-[(3-methyl-phenyl)amino]-7-[2-((R)-6-methyl-2-oxo-morpholin-4-yl)-ethoxy]-6-[(vinylcarbonyl)amino]-quinazoline (9) 4-[(3-chloro-4-fluoro-phenyl)amino]-7-{2-[N-(2-oxo-tetrahydrofuran-4-yl)-N-methyl-amino]-ethoxy}-6-[(vinylcarbonyl)amino]-quinazoline

(10) 4-[(3-chloro-4-fluoro-phenyl)amino]-7-{ 3-[N-(2-oxo-tetrahydrofuran-4-amino]-propyloxy}-6-[(vinylcarbonyl)amino]-quinazoline

EXAMPLE 3

Coated tablets containing 75 mg of active substance 1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable apparatus and mixed with the rest of the magnesium stearate. This granulate is compressed in a tablet-making machine to form tablets of the desired shape.

Weight of core: 230 mg

Die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 4

Tablets containing 100 mg of active substance

Composition 1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 5

Tablets containing 150 mg of active substance

Composition 1 tablet contains:

|  |  |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
|  | 300.0 mg |

Preparation

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE 6

Hard gelatine capsules containing 150 mg of active substance 1 capsule contains:

|  |  |
|---|---|
| active substance | 50.0 mg |
| corn starch (dried) approx. | 80.0 mg |
| lactose (powdered) approx. | 87.0 mg |
| magnesium stearate | 3.0 mg |
| approx. | 420.0 mg |

Preparation

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE 7

Suppositories containing 150 mg of active substance 1 suppository contains:

|  |  |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
|  | 2,000.0 mg |

Preparation

After the suppository mass has been melted the active substance is homogeneously distributed therein and the melt is poured into chilled moulds.

EXAMPLE 8

Suspension containing 50 mg of active substance 100 ml of suspension contain:

|  |  |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100 ml |

Preparation

The distilled water is heated to 70° C. The methyl and propyl p-hydroxybenzoates together with the glycerol and carboxymethylcellulose sodium salt are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 9

Ampoules containing 10 mg active substance

Composition

|  |  |
|---|---|
| active substance | 10.0 mg |
| 0.01N hydrochloric acid q.s. |  |
| double-distilled water ad | 2.0 ml |

Preparation

The active substance is dissolved in the necessary amount of 0.01 N HCl, made isotonic with common salt, filtered sterile and transferred into 2 ml ampoules.

EXAMPLE 10

Ampoules containing 50 mg of active substance

Composition

|  |  |
|---|---|
| active substance | 50.0 mg |
| 0.01N hydrochloric acid q.s. |  |
| double-distilled water ad | 10.0 ml |

Preparation

The active substance is dissolved in the necessary amount of 0.01 N HCl, made isotonic with common salt, filtered sterile and transferred into 10 ml ampoules.

EXAMPLE 11

Capsules for powder inhalation containing 5 mg of active substance 1 capsule contains:

|  |  |
|---|---|
| active substance | 5.0 mg |
| lactose for inhalation | 15.0 mg |
|  | 20.0 mg |

Preparation

The active substance is mixed with lactose for inhalation. The mixture is packed into capsules in a capsule-making machine (weight of the empty capsule approx. 50 mg).

weight of capsule: 70.0 mg size of capsule=3

EXAMPLE 12

Solution for inhalation for hand-held nebulisers containing 2.5 mg active substance 1 spray contains:

| | |
|---|---|
| active substance | 2.500 mg |
| benzalkonium chloride | 0.001 mg |
| 1N hydrochloric acid q.s. | |
| ethanol/water (50/50) ad | 15.000 mg |

Preparation

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges). Contents of the container: 4.5 g

What is claimed is:

1. A compound of the formula

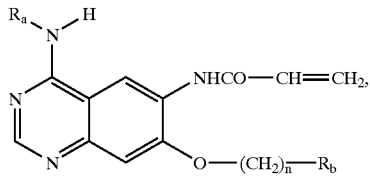

(I)

wherein $R_a$ denotes a benzyl or 1-phenylethyl group or a phenyl group substituted by the groups $R_1$ and $R_2$, wherein $R_1$ denotes a hydrogen, fluorine, chlorine or bromine atom, a methyl, trifluoromethyl, cyano or ethynyl group and $R_2$ denotes a hydrogen or fluorine atom, $R_b$ denotes an —N(CH$_2$CO$_2$R$_3$)$_2$-group, wherein $R_3$ denotes a hydrogen atom, a methyl or ethyl group;

a R$_4$O—CO—CH$_2$—N—CH$_2$—CH$_2$—OH group optionally substituted at the methylene groups by 1 or 2 methyl or ethyl groups, wherein $R_4$ denotes a hydrogen atom or a $C_{1-4}$-alkyl group;

a 2-oxo-morpholin-4-yl-group which may be substituted by 1 or 2 methyl or ethyl groups; or a N-(2-oxo-tetrahydrofuran-4-yl)-methylamino-group and n denotes an integer in the range from 2 to 4, or a tautomer or salt thereof.

2. A compound of the formula I according to claim 1, wherein $R_a$ denotes a benzyl or 1-phenylethyl group or a phenyl group substituted by the groups $R_1$ and $R_2$, wherein $R_1$ denotes a hydrogen, fluorine, chlorine or bromine atom, a methyl, trifluoromethyl, cyano or ethynyl group and $R_2$ denotes a hydrogen or fluorine atom, $R_b$ denotes an —N(CH$_2$CO$_2$R$_3$)$_2$-group, wherein $R_3$ denotes a hydrogen atom, a methyl or ethyl group, a R$_4$O—CO—CH$_2$—N—CH$_2$—CH$_2$—OH group optionally substituted at the methylene groups by 1 or 2 methyl or ethyl groups, wherein $R_4$ denotes a hydrogen atom or a $C_{1-4}$-alkyl group, a 2-oxo-morpholin-4-yl-group which may be substituted by 1 or 2 methyl or ethyl groups, or a N-(2-oxo-tetrahydrofuran4-yl)-methylamino-group and n denotes an integer in the range from 2 to 4, with the exception of the compound 4-[(3-bromophenyl)amino]-7-[3-(2-oxo-morpholin-4-yl) propyloxy]-6-[(vinylcarbonyl)amino]-quinazoline, or a tautomer or salt thereof.

3. A compound of the formula I according to claim 1, wherein $R_a$ denotes a 1-phenylethyl group or a phenyl group substituted by the groups $R_1$ and $R_2$, wherein $R_1$ denotes a fluorine, chlorine or bromine atom, a methyl or ethynyl group and $R_2$ denotes a hydrogen or fluorine atom, $R_b$ denotes a 2-oxo-morpholin-4-yl-group which is substituted by 1 or 2 methyl or ethyl groups, or a N-(2-oxo-tetrahydrofuran-4-yl)-methylamino-group and n denotes an integer from the range from 2 to 4, or a tautomer or salt thereof.

4. A compound of the formula I according to claim 1, wherein $R_a$ denotes a 1-phenylethyl- or 3-chloro-4-fluorophenyl group, $R_b$ denotes a 2-oxo-morpholin-4-yl-group which is substituted by 1 or 2 methyl groups, and n denotes an integer from the range from 2 to 4, or a tautomer or salt thereof.

5. A compound selected from the group consisting of:

(1) 4-[(R)-(1-phenyl-ethyl)amino]-7-[2-(2,2-dimethyl-6-oxo-morpholin-4-yl)-ethoxy]-6-[(vinylcarbonyl)amino]-quinazoline, (2) 4-[(3-chloro-4-fluoro-phenyl)amino]-7-[3-((S)-6-methyl-2-oxo-morpholin-4-yl)-propyloxy]-6-[(vinylcarbonyl)amino]-quinazoline, (3) 4-[(3-chloro-4-fluoro-phenyl)amino]-7-[3-(2,2-dimethyl-6-oxo-morpholin-4-yl)-propyloxy]-6-[(vinylcarbonyl)amino]-quinazoline, (4) 4-[(3-chloro-4-fluoro-phenyl)amino]-7-[2-(2,2-dimethyl-6-oxo-morpholin-4-yl)-ethoxy]-6-[(vinylcarbonyl)amino]-quinazoline, (5) 4-[(3-chloro-4-fluoro-phenyl)amino]-7-[3-((R)-6-methyl-2-oxo-morpholin-4-yl)-propyloxy]-6-[(vinylcarbonyl)amino]-quinazoline, (6) 4-[(3-chloro-4-fluoro-phenyl)amino]-7-[2-((R)-6-methyl-2-oxo-morpholin-4-yl)-ethoxy]-6-[(vinylcarbonyl)amino]-quinazoline, (7) 4-[(3-chloro-4-fluoro-phenyl)amino]-7-[2-((S)-6-methyl-2-oxo-morpholin-4-yl)-ethoxy]-6-[(vinylcarbonyl)amino]-quinazoline, (8) 4-[(3-chloro-4-fluoro-phenyl)amino]-7-[4-((S)-3-methyl-2-oxo-morpholin-4-yl)-butyloxy]-6-[(vinylcarbonyl)amino]-quinazoline and (9) 4-[(3-chloro-4-fluorophenyl)amino]-7-[$^4$-((R)-6-methyl-2-oxo-morpholin-4-yl)-butyloxy]-6-[(vinylcarbonyl) amino]-quinazoline, or a tautomer or salt thereof.

6. A physiologically acceptable salt of a compound according to claim 1, 2, 3, 4 or 5, formed with an inorganic or organic acid or base.

7. A pharmaceutical composition comprising a compound according to claim 1, 2, 3, 4 or 5 or a pharmaceutically acceptable salt thereof and a pharmaceutically acceptable carrier or diluent.

8. A method of treating a benign or malignant tumour, a disease of the respiratory tract or lungs, polyps, a disease of the gastrointestinal tract, bile duct or gall bladder, a disease of the kidneys or of the skin, which comprises administering a therapeutically effective amount of a compound according claim 1, 2, 3, 4 or 5 or a pharmaceutically acceptable salt thereof.

* * * * *